United States Patent [19]
Graham

[11] 4,043,176
[45] Aug. 23, 1977

[54] ACOUSTIC WHITE NOISE GENERATOR

[75] Inventor: Lloyd J. Graham, Newbury Park, Calif.

[73] Assignee: Rockwell International Corporation, El Segundo, Calif.

[21] Appl. No.: 697,818

[22] Filed: June 21, 1976

[51] Int. Cl.$^2$ ............................................. G01N 29/00
[52] U.S. Cl. ................................ 73/1 DV; 73/67.5 R; 73/88 R
[58] Field of Search ......... 73/1 DV, 71.5 US, 67.5 R, 73/88 R; 181/142; 331/78, 177 V

[56] References Cited
U.S. PATENT DOCUMENTS 3,967,143   6/1976   Watanabe et al. ..................... 310/8.1

OTHER PUBLICATIONS

Fowler, K. A., Acoustic Emission Simulation Test Set. From Materials Research and Standards, Mar. 1971, pp. 35, 36.

Primary Examiner—Jerry W. Myracle
Attorney, Agent, or Firm—L. Lee Humphries; Craig O. Malin

[57] ABSTRACT

A narrow banded acoustic transducer is driven by a VCFO whose output is varied by input signals of variable amplitude. One can simulate acoustic emissions for purposes of calibrating transducers which monitor a structural part for such emissions. Different signals for the control of the VCFO are generated to provide for specific test pulses.

5 Claims, 15 Drawing Figures a b c d e f g h i

ACOUSTIC WHITE NOISE GENERATOR

BACKGROUND OF THE INVENTION

The present invention relates to the generation of acoustic waves and more particularly, the invention relates to the reproducible production of high frequency noise bursts.

The generation of acoustic signals has become increasingly important for the detection of flaws and defects in structural parts. Ultrasonic signals and particularly pulses are caused to traverse the material, and the interaction thereof with the acoustic waves is used to obtain information on the uniformity of texture (or lack of it) of the material. It is apparent that the resolution of this detection method depends on the wave length of the acoustic signal. Thus, it is desirable to operate with as high a frequency as possible to permit the detection of minute cracks and fissures.

Another field of applying acoustics to flaw detection relates to acoustic emissions. These are spontaneous, high frequency acoustic waves emitted upon relief of localized tension and stress in the structural part. The emission of these waves can be used as a criterion to indicate the internal development of a crack, fissure or the like. It is inevitable that during the continuous monitoring of acoustic emissions in a structure noise is also picked up from non-relevant sources. This noise can be similar in many ways to the acoustic emissions generated by a growing crack, and it is a particularly vexing problem to identify an acoustic emission and separate it from the noise. One characteristic which is used to accomplish this is their frequency spectrum. Identification and interpretation of acoustic emissions from their spectrum relate directly to the calibration of the monitoring pickup transducers and of the various wave propagation paths in the structure under test. It was found that the existing devices for producing bursts of acoustic energy for purposes of calibration are either too narrow banded or afford little control over their frequency spectrum.

DESCRIPTION OF THE INVENTION

It is an object of the present invention to provide a new and improved source for high frequency, ultrasonic signals.

It is another object of the present invention to provide for a new and improved method of acoustic signal generation and transmission in structural parts to be tested in the general sense with regard to flaws.

It is a specific object of the present invention to provide a new and improved acoustic wave generator for producing reproducible bursts of acoustic energy to be used, e.g. for calibrating transducers which are provided for monitoring a structural part for acoustic emissions.

In accordance with the preferred embodiment of the present invention, it is suggested to use a solid state electrically controlled transducer (ferroelectric or piezoelectric) which provides acoustic signals in response to an electrical signal being provided by a voltage-controlled frequency oscillator which, in turn, is controlled by a signal and wave form generator being preferably of the variety which provides particularly contoured voltage signals on a repetitive or, at least, repeatable basis.

The VCFO-transducer combination is capable of providing a well-defined spectrum which is narrow-banded in each instance, but the narrow emission band is shifted over a wide range of frequencies for corresponding variable inputs to the VCFO, and for each burst or chirp being produced. The narrow bandedness of such a burst or chirp results from the transducer emission spectrum provided for a particular input voltage for the VCFO; the broadbandedness results from the range of voltages covered by the input signal as generated and applied to the VCFO.

An additional parameter in the general sense is the time sequence of the voltage variations for the input of the VCFO. The same amplitude range may well be covered by differently contoured voltage pulses, but the acoustic signal generated and/or picked up at a remote location will be quite different in these instances. It was found particularly that by suitably contouring the wave shape of a voltage pulse applied to the VCFO input one can simulate readily a variety of acoustic emissions. It was also found that by suitably contouring the wave shape of the VCFO input one can correct or modify the particular response characteristics of a pickup transducer because these characteristics may exhibit certain irregularities. It is important that for each field of application, the frequency spectrum of the generated acoustic signals is well controlled which is particularly important for the megahertz range of acoustic frequencies because relatively little direct interference from outside sources can be expected at such high frequencies so that broad band control per se may provide valuable information, at least in some instances.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows an electro-acoustic transducer 10, which generates acoustic waves in direct response to electrical input signals. The transducer 10 includes a housing 11 in which the outer conductor 12 of a coaxial connection 13 ends and is terminated. The bottom of the transducer housing 11 includes a metallic, ceramic, or plastic wafer 14 covering a ferroelectric or piezoelectric disk 15. The disk 15 may, for example, be of lead metaniobate or lead zirconate-titanate or PZT for short. A specific material which is quite useful here is traded under the designation PZT-5A. The disk 15 has its top and bottom covered with silver coatings serving as electrodes. One of these electrodes connects to the housing 11 assuming its potential (as reference) while the top electrode 16 is connected to the inner conductor of the coaxial cable. The disk 15 is acoustically loaded by a body 17 made of rubber in which metal particles have been dispersed.

Figure 1:
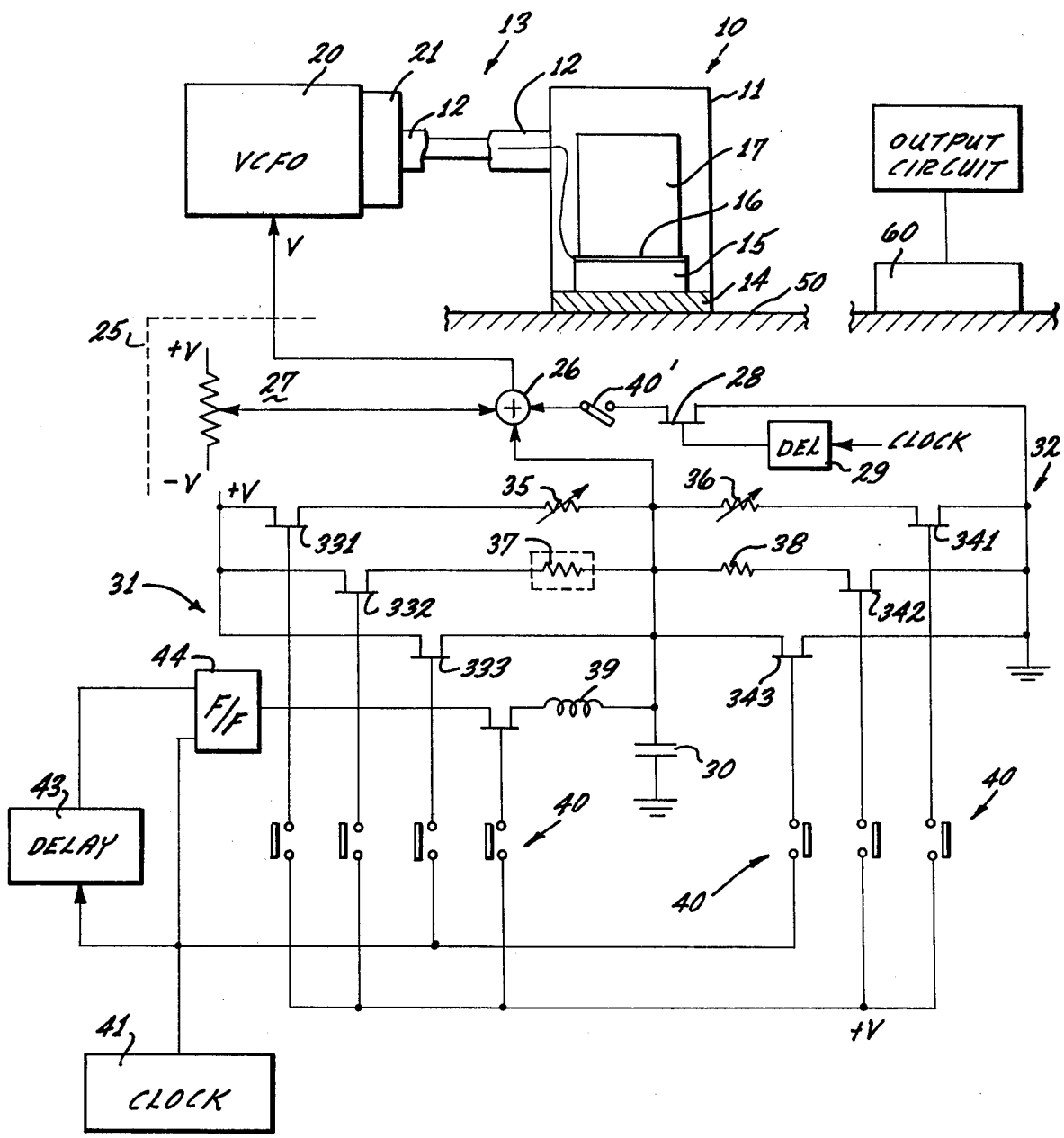
FIG. 1 is a somewhat schematic view, including a circuit diagram of equipment for reproducibly producing ultrasonic bursts and applying them to a part to be tested or supervised.
Figure 2:
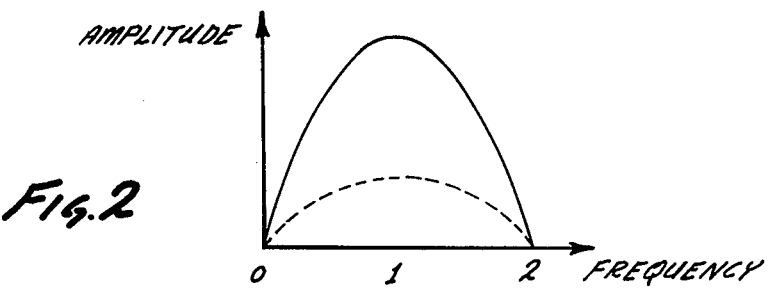
FIG. 2 is a frequency response characteristic of a transducer used in the equipment shown in FIG. 1.

The transducer as depicted in FIG. 1 has a frequency response shown as a solid line curve in FIG. 2, the center peak frequency being, for example, at 1 MHz or thereabouts, with litle or no response for frequencies higher than about twice that value. This specific response has validity for steady signals at any of the frequencies within the plotted range. However, the same or about the same curve is valid for sweep or sweep-like signals in which the frequency varies rather slowly, for example, at a rate of one gigahertz per second or less. Thus, the plotted frequency response as to each frequency has validity for stationary inputs or quasi stationary inputs as regards to such frequency.

The situation is different for fast changes in frequency. The dotted curve in FIG. 2 is representative of an amplitude vs. frequency response in which the frequency changes much faster. Fast, in this context, is to mean a noticeable change in frequency from cycle to cycle or, to put it differently, the rate of change in frequency becomes comparable to the frequency itself. An inherent delay in the transducer operation causes, in fact, the response to flatten.

The transducer 10 is coupled to a solid object 50 such as a structural part and transmits thereto acoustic signals. These acoustic signals propagate through the object serving as transmission medium and are picked up at a location (or several spaced-apart locations) being remote from the point of transmission. A transducer 60 is coupled to the object 50 for this purpose and picks up any acoustic signals arriving at the (physical) interface of transducer 60 and object 50. The acoustic signal as picked up by the transducer 60 is converted therein into an electrical signal which is passed through an output circuit for example, for further study. Details of the pickup are conventional and do not constitute per se a part of the invention.

The object 50 as illustrated may represent a variety of structures. Moreover, the present invention can be explained fully with respect to different modes of operation which may be practiced on the same object. By way of example, the object 50 may be a stainless steel pressure vessel for use in a chemical process plant. The vessel may be 8 ft. in diameter, 10 ft. tall, and may have a wall which is about one half inch thick. Alternatively, the vessel may have a diameter of 10 ft., a height of 111 ft., and a wall being about 5 inches thick and made of, for example, a low alloy steel covered with a 4 inch thick layer of thermal insulation.

Such a structural part can be expected to be tested acoustically in a two-fold manner. The first test is carried out prior to use and involves the determination of the attenuation and dispersion characteristics of typical propagation paths in the structure. In such a case, acoustic signals are generated by the transducer 10, and the signal picked up by transducer 60 is indicative of these characteristics. Subsequently, the structure 50 is continuously monitored during proof load and service load conditions and the material may undergo local stress relief with concomitant emission of bursts of acoustic waves. Some of these acoustic emissions may be quite harmless; others may indicate the beginning of the formation of a crack. Most prominently, however, the emission of such acoustic bursts by the material from the same location may well indicate the growth of a crack which has to be detected. Particularly for the latter case the supervising transducer requires calibration in order to distinguish such acoustic emissions from other noise. In this case then the transducer 10 can also serve as a source for acoustic calibration signals. Thus, the transducer 60 may be interpreted as being one of those transducers whose response in this particular environment and for this particular purpose, namely detection of acoustic emissions, requires calibration.

Generally speaking, however, transducer 60 will be of that kind that is needed or wanted for a specific purpose. This aspect should be born in mind because the transducer 10 will be operated to provide signals adapted to the specific use that is desired, and different specific uses require only a change in the signal that is applied to transducer 10. The pickup transducers may differ as to structure in each instance of use.

Proceeding now with the description of the system, the coaxial connection 13 is connected to output terminals of a voltage controlled frequency oscillator 20 or VCFO for short. The oscillator 20 is of conventional design and produces a narrow band of output frequencies for a particular input signal, usually being d.c. The frequency band may, for example be about 30 KHz wide, but the generator covers a much wider range. For example, the generator 20 may produce no noticeable output for 0 input voltage and a maximum frequency of, for example, 10 MHz for an input of +V.

The VCFO 20 may have an output circuit which includes a particular, low pass filter 21 which cuts off frequencies above a particular desired range, for example, 2 MHz. Thus, no signal above that frequency is transmitted to the acoustic signal transmitting transducer 10. As will be understood shortly, the use of this lowpass filter 21 is a suitable expedient for the convenient formation of pulses and bursts.

It can readily be assumed that the relationship between the input voltage V for the VCFO 20 and its output frequency $f$ is a linear one, i.e., $dV/df =$ constant. However, this is not a necessary requirement as any non-linearity can be compensated in the particular stage which generates the input wave form for the VCFO and which will be described next.

The input signal for the VCFO is generated by a wave form generator 25. The wave form generator can be constructed in a variety of ways, and are commercially available, including generators with digital memory chips for producing particular wave and pulse forms. However, the following analog representation for obtaining a specific variety of wave forms will suffice for explanatory purposes. By way of example, generator 25 includes a capacitor 30, a charge control circuit 31, and a discharge control circuit 32. The charge control circuit includes a plurality of electronic switches such as FETs 331, 332, by means of which different impedances, e.g. resistors, such as 35 and 37, can be connected between the capacitor 30 and a voltage source, for example, +V.

The set of impedances includes also an inductance 39, but its connection to +V is an indirect one as will be explained below. One particular circuit connection that can be completed by a FET, 333, does not include a resistor at all to symbolize a low impedance, rapid charge circuit for the capacitor 30 when the respective FET is gated on.

The discharge circuit 32 includes also a plurality of FETs, 341, 342, and 343, to place discharge resistors such as 36 and 38 or no resistor between ground potential and the capacitor 30.

The number of resistors in the charge and discharge circuits shown here by way of example, is not limited to the particular number illustrated, but the number of resistors is simply representative of a variety of different wave forms to be generated.

The switches 331 etc. and 341 etc. are under control of a wave form selector 40 which may include a dial or the like for purposes of selecting charge and discharge impedances in order to produce a desired wave form. The FETs 331, 332, 341 and 342, providing switching signal for non-zero charge or discharge resistances, are gated on by the respective selection switch for the duration of the selection. The low (zero) impedance charge and discharge portions in circuit 31 and 32 will be controlled in that the respective selector switches connect a clock 41 to the gate of the respective FET, 333 or 343, to obtain a brief turn-on pulse for producing a rapid charge or discharge of the capacitor 30 as desired.

Usually, the selection will be made so that for a selected non-zero impedance in the charge circuit the capacitor 30 will be discharged rapidly with the clock via 343 while on the other hand, a rapid charge of the capacitor by clock control and via 333 is followed by a gradual discharge through a selected non-zero impedance in the discharge circuit 32. The clock 41 determines the repetition rate of the production of wave forms and pulses that make up the effective wave form signals for driving the VCFO 20. Typically, the clock may produce pulses at a rate of 200 Hz but of a very short duration.

One of the impedances in the charge circuit 31 is the coil 39 which completes an oscillating circuit when connected to capacitor 30. The coil when so connected receives a voltage pulse at the rate of the clock, but at a selectively adjustable delay to each normal clock pulse. This will provide an oscillatory voltage across the capacitor until such time the respective next clock discharges the capacitor to ground. For example, circuit 43 may provide an adjustable delay for the clock pulse to set a flip-flop 44 and the next clock resets it. That flip-flop provides a voltage to the coil 39 for the duration of the set state. The reset state provides ground to the coil so that upon occurrence of each clock, capacitor and coil are both grounded across all terminals. This way, one obtains a wave form of an oscillatory nature followed by a pause.

The capacitor 30 has its non-ground electrode connected to a summing poing 26 whose output is the output proper of the wave form generator 25 and is applied to the control voltage input of VCFO 20. In addition to the capacitor signals, summing point 26 receives an adjustable bias from a circuit 27, the bias being variable between $-V$ and $+V$. It can thus be seen that the various signals generated across the capacitor 30 are combined with the adjusted bias to select the particular signal configuration and wave form that is being applied to the VCFO 20.

FIG. 1 shows also an additional bias for summing point 26. A FET 28 does not clamp the output of summing point 26 to ground or a negative potential for the duration of the astable state of a monostable device 29, being operated by the clock, i.e., in the beginning of each wave form pulse. After the monostable device 29 is run, the FET 28 is rendered conductive and holds the signal input for the VCFO 20 to ground. This additional bias may be used in lieu of or in addition to filter 21 for the generation of the trailing edge of the pulses applied to VCFO 20.

Figure 3:
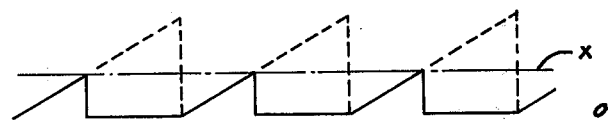
FIG. 3a through 3i are diagrams for real and virtual wave forms generated in and used by the equipment shown in FIG. 1.
Figure 3:
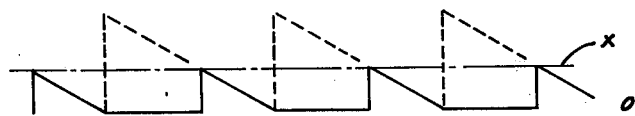
Figure 3:
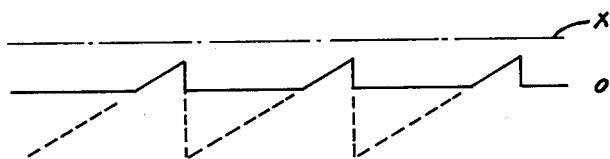
Figure 3:
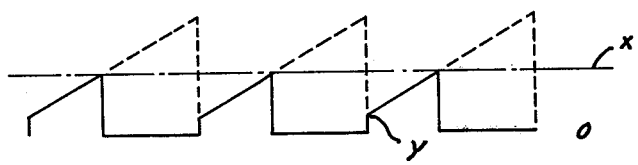
Figure 3:
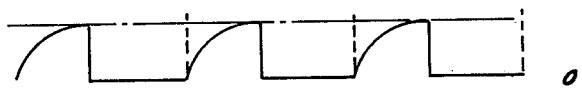
Figure 3:
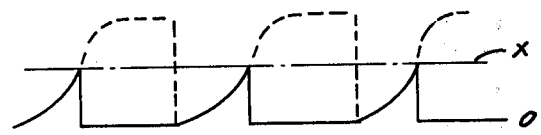
Figure 3:
Figure 3:
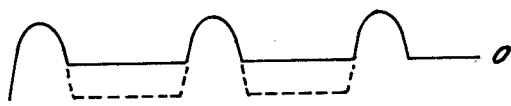
Figure 3:
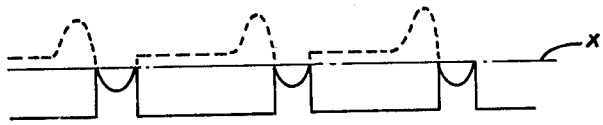

The FIGS. 3 depict a plurality of wave forms generated by the wave form generator 25 which provides the input for the VCFO 20 via the summing point 26 in conjunction with biasing circuit 27. In each instance of FIG. 3, the wave form proper generated and developed at the output of summing point 26 is drawn in a dashed line. The range of voltages covered thereby is, however, in most instances, extended beyond the particular range operative for producing frequencies that actually drive the transducer 10. The lower boundary for this whole range is given by zero volts for the input of VCFO 20 so that all negative voltages applied thereto remain ineffective. On the other hand, the low-pass filter 21 cuts off frequencies above the 2 MHz range limit so that any voltage applied to VCFO 20 and having a value $x$ or larger will produce an output frequency higher than 2 MHz. Therefore, such a voltage $> x$ will actually remain ineffective, as far as the output of circuits 20 and 21 is concerned.

Each of the FIG. 3 includes a solidly drawn curve which will be called a virtual wave form signal. This virtual wave form represents the equivalent voltage value and contour which would produce the same VCFO output as the VCFO plus filter combination produces by operation of the actual (dashed) input for the VCFO. Generally speaking, the virtual wave form differs from the actual or real wave form as produced by circuit 25 in that the virtual wave signal is zero for all negative values of the actual wave form and for values above the particular value $x$ resulting in VCFO frequencies above the cutoff range of filter 21.

Referring first to FIG. 3a, the figure shows the wave form generated when the bias circuit 27 is adjusted to zero volts, and when the wave form generator 25 is in a select state in which a relatively high impedance is effective in the charge circuit 31 (FET 331 being on), while the clock 41 turns on briefly FET 343 to reset and discharge the capacitor 30 periodically. The charge control circuit is permanently on for the duration of the generation of this particular wave form, for the periodicity of the generated wave form results from the clock controlled discharge.

Whenever the sweep signal traverses, the level denoted $x$ the resulting high frequency output of VCFO 20 is suppressed by low-pass filter 21 so that the output signal of the latter drops to zero. Consequently, the signal applied to and driving transducer 10 is composed of individual bursts or chirps which begin with the lowest possible frequency VCFO 20 can actually produce (such devices usual produce a noticable output only above a few KHz). The frequency increases to 2 MHz whereupon the transducer driver signal actually drops to zero until the next clock pulse resets the sweep circuit for the next burst to begin.

Figure 4A:
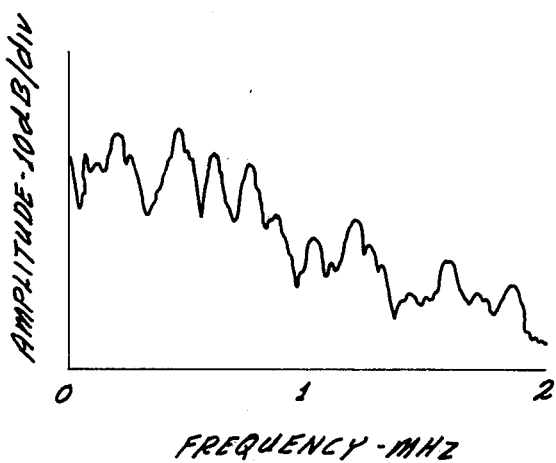
FIGS. 4a to 4d are various frequency spectra of acoustic signals produced by and picked up by equipment shown in FIG. 1 and (except FIG. 4c) resulting from pulses as per several of the FIGS. 3, the four graphs each have a logarithmic amplitude scale (ordinate) and a linear frequency scale (abscissa).

FIG. 4a illustrates the frequency spectrum of a burst when received by transducer 60 in response to a burst produced by transducer 10 when receiving a wave form as per FIG. 3a.

FIG. 3b denotes a situation in which the charge circuit for capacitor 30 is clock pulse controlled (FET is on with the clock) and applies a voltage pulse $+V$ to the capacitor 30 as a high charge pulse of short duration. The discharge circuit 32 may be adjusted for high impedance discharge via resistor 36 and FET 341. Again, the solidly drawn curve is the effective, virtual ramp signal. Thus, each sweep begins at a level well above the level x so that for a relatively long period of time, the VCFO output has frequency above the 2 MHz range, and these oscillations are cut off by the filter 21 so that stimulating signals are not applied to the acoustic wave transducer 10.

As soon as the output of summing point 26 traverses the level x, a 2 MHz signal corresponding to an upward jump in the virtual wave form curve is produced, and as the ramp signal slopes down further, the frequency of the transducer driver signal decreases accordingly until traversing the near zero level. The bias in circuit 27 may be adjusted so that the zero level will be traversed prior to the next clock which produces a new charge pulse for capacitor 30 in this case. Thus, transducer 10 provides oscillation bursts at a chirp rate of 200 Hz, and each burst or chirp begins at 2 MHz and drops to zero frequency followed by a pause until another burst is produced.

It can readily be seen that, for example, in the cases of FIGS. 3a and 3b and, as will be shown in other cases, the clock pulse operation could be replaced by an amplitude response in that upon obtaining a particular charge state (or discharge state) the capacitor discharge or re-charge is being triggered. In this case, the wave form generator includes its own oscillator being of the blocking oscillator variety. However, one can readily see that such incorporation of the clocking operation may not be practical because it is advisable to control the periodicity of the bursts separately by a particular clock and without trying the repetition rate of the bursts to the ramp slope because that slope determines the rate of change in frequency of an acoustic wave burst and should be treated as an independent parameter. The resistances 35 and 36 in the respective high impedance charge or discharge circuit are drawn to be adjustable in FIG. 1 which is indicative of the possibility and desirability of varying the slope of the ramp signals.

FIG. 3c depicts a situation in which the wave form generator 25 is adjusted as indicated in FIG. 3a. However, the bias circuit 27 is adjusted to apply a strong negative value to summing point 26. Now, only the peak portions of the range become effective. It can readily be seen that by appropriate fine tuning or fine trimming of the bias 27, the frequency range of each burst is controlled as to the highest frequency produced. The clock causes discharge of the capacitor 30 when, for example, the output of the summing point 26 has reached a value causing VCFO 20 to produce an output of 1 MHz. In this case then, only the lower frequency range from zero to 1 MHz is included in each acoustic burst.

FIG. 3d illustrates a different situation resulting from biasing the summing point 26 to a more positive level. In this case, the output of summing point 26 will never drop to zero, but the ramp voltage retraces when the output of summing point 26 has dropped to a value for which the VCFO 10 produces a non-zero frequency such as, for example, 1 MHz. As the ramp slopes up, the frequency rises and the filter 21 cuts off any output when the 2 MHz level is being traversed so that the virtual ramp drops again to zero until the clock discharges the capacitors 30 and the ramp begins a new cycle.

It should be noted that most of the pulses in FIG. 3 are shown to have about similar width. However, it can readily be seen that by changing, e.g. the slope of the ramp, the pulse width is varied therewith. If one wants to maintain the pulse length, but the slope of the ramp is still to be varied, one needs to use circuit 28, 29. Use of this circuit obviates the distinction between virtual and real ramps as the termination of a pulse through clamping action by circuit 28, 29 is directly effective and may supersede the filter cut off action if occurring at ramp signal levels below x.

Upon adjustment of the delay, monostable multivibrator 29, one can vary the length of the pulse, particularly to obtain cut off below the level x if that is desired. In other words, an up sloping ramp signal can be clamped to ground potential before it reaches the level x. This is particularly of interest for a wave form, as per FIG. 3d. This wave form is to be used to obtain a more or less narrow band within each burst. The resistance 35 in the charge of the wave form generator circuit determines the slope of each pulse as between onset and end which, in turn, controls the band width of each burst. The selected bias 27 permits slicing a particular portion of the total band in that the low point of ech ramp (point 4) is determined by the bias and that, in turn, determines the lowest frequency of a burst produced. Without circuits 28, 29, the upper band limit will always be 2 MHz. However, if the delay 29 is adjusted for an earlier termination of the ramp (by clamping the output of the summing point 26 to ground), the upper frequency limit of that band is adjusted therewith. In other words, a termination of each pulse, e.g. at times $t$, shifts the highest amplitude of each pulse as actually being produced to a lower level $z$, and the amplitude differential between $y$ and $z$ determines the frequency band actually being used upon selecting the ramp-slope-defining impedance to have a very high value, one can obtain a very narrow band in each chirp.

It will be appreciated that the wave forms as per FIGS. 3c and 3d result from the same selection of impedances as in the case of FIG. 3a except that the bias 27 is shifted to a more negative or to a more positive value. Analogously, more negative or positive bias for a selection that causes a wave form as per FIG. 3b, results in the production of virtual signals and wave forms analogous to FIGS. 3c and 3d, respectively, except that the signal level decreases during each pulse corresponding to a gradual reduction in frequency of the transducer drive signal.

FIG. 3e shows a pulse diagram which is modified as compared with FIG. 3a in that resistor 35 is adjusted to a rather low value. The charge curve of capacitor 30 follows the usual non-linear $e$ function with negative exponent. The wave form still traverses the level $c$ in which the cutoff of filter 21 becomes effective.

FIG. 3f depicts a situation in which the selected resistor, for example, 37 when selected for operative connection in charge circuit 31 has a non-linear impedance. It is assumed that this particular resistor has a characteristic in which its resistance is, in fact, negative for most of its effective range. The resistance value may level off for higher values or it may be advisable to limit current flow through the resistor otherwise.

Actually, block 37 should be interpreted as an adjustable non-linear resistance network. The particular wave form of FIG. 3g results from a different pattern of resistances in the charge circuit and will be used to obtain a near constant output for the acoustic waves. The rate $dV/df$ is small for low frequencies as well as for frequencies near 2 MHz, but high for frequencies of say about 1 MHz. The faster rate of change in the wave form of each pulse at levels for the production of frequencies near 1 MHz has the effect that the output of the transducer 10 is lower than in the steady or quasi stationary state. Thus, this wave shape provides for a transition from the solid curve to the dashed curve in FIG. 2.

FIGS. 3h and 3i depict two different situations when the charge circuit for capacitor 30 is supplemented by the coil 39 and a stimulating pulse is applied for an adjustable delay prior to the respective next clock pulse. FIG. 3h in particular depicts a situation in which that delay 43 is adjusted to cover just above one half wave of an oscillation for a particularly adjusted value of the coil 39. At the end of such a half wave, the clock pulse sets the capacitor circuit to the zero level. Bias 27 is shifted to a more negative level. The FIG. 3g, therefore, can be interpreted as producing a wave form in which the peak portion of a sine wave is used to produce a double ramp, i.e., a more or less gradual upswing followed by a gradual downswing so that in effect the frequency spectrum from zero to a peak frequency, being equal to or below 2 MHz, is run through twice for each pulse.

Figure 4B:
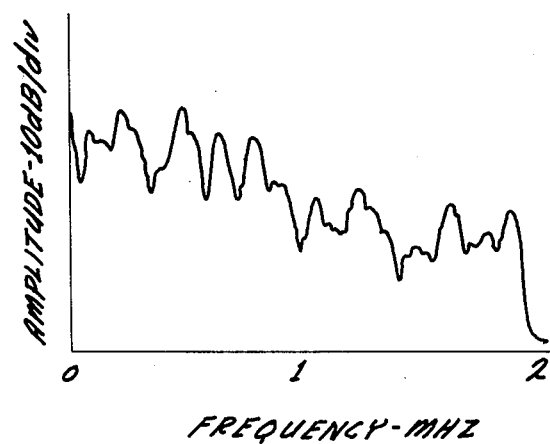

FIG. 4b illustrates the frequency spectrum of a burst when received by transducer 60 in response to an acoustic burst produced by transducer 10 in response to a wave form as per FIG. 3h. It should be noted that the spectrum is richer in higher frequencies as compared with FIG. 4a (wave form FIG. 3a).

FIG. 3i depicts the situation in which the delay, provided by circuit 43, is somewhat larger to cover a full oscillation which, however, has a lower frequency, coil 39 having been adjusted accordingly. The biasing circuit 27 has been adjusted so that most portions of the output of summing point 26 is above level x. Thus, only the bottom peak of the negative half wave has values below the x level, so that only frequencies from a certain minimal, non-zero value, up to 2 MHz, are produced for and by each pulse.

Figure 4C:
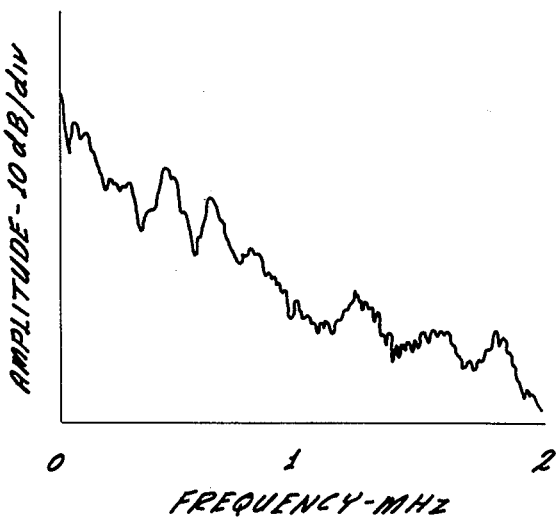
Figure 4D:
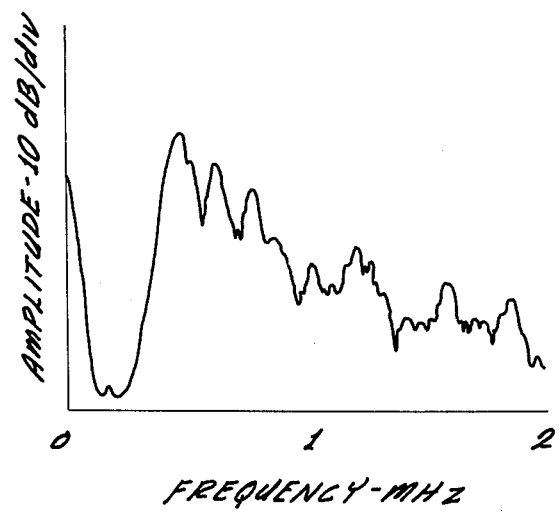

Turning now to the calibration operation for transducer 60 in that the latter has to respond to acoustic emissions of the object 50. For example, the internally developing cracks, i.e., the local relief of localized tension produces micro-noise having a rather low level and very high frequencies. Although acoustic emissions produced under different conditions can have a wide variety of frequency spectral types, it was found that a typical acoustic emission burst has a frequency spectrum as shown in FIG. 4c. This frequency spectrum has resulted from the detection of a known acoustic emission followed by frequency analysis by means of suitable, known instrumentation. This particular spectrum includes, of course, the frequency selectivity of the transducer 60. For purposes of calibration, it is desirable to duplicate that spectrum. Thus, acoustic signals are to be produced which simulate that spectrum. A good simulation is shown in FIG. 4d, showing the response of such a transducer to a particular acoustic signal which was generated by applying to the VCFO a voltage signal as shown in FIG. 3i.

It can, thus, be seen that the frequency spectrum of the bursts as received by the pickup transducer 60 can be modified by modifying the wave form of the signal that drives the VCFO 20. In each instance the control signal for the latter results in a narrow band output by the VCFO whose output frequency varies over a wide range so that the narrow band itself is shifted over that wide range. That range is determined by the boundaries (amplitude limits) of the signal driving the VCFO. The various wave forms and contour modify the sequence (or direction) in which the various frequencies are run through. So far as calibrating operations are concerned, one can readily see, that visual inspection of a frequency spectrum and variations in the parameters determining the signal contour as provided by and in generator 25 permits matching of desired particular spectra.

The invention is not limited to the embodiments described above but all changes and modifications thereof not constituting departures from the spirit and scope of the invention are intended to be included.

I claim:

1. An acoustic white noise generator, comprising:
   a transducer which includes a solid state element and electrical electrodes coupled to the element and providing acoustic oscillations in response to an electrical a.c. signal applied to the electrodes;
   a signal controlled frequency oscillator coupled to said electrodes and providing the electrical a.c. signal having frequency depending upon an input signal applied to the oscillator to obtain said acoustic oscillations of similar frequency and within a relatively narrow band; and
   an electric signal generator providing at least one electrical signal of particular amplitude-variable shape and connected to the oscillator to provide the voltage signal thereto for serving as said input signal to obtain a variable frequency burst resulting in a variable frequency acoustic burst from said transducer.

2. An acoustic generator as in claim 1 where said signal generator includes means for providing the electrical signal on a periodic basis, resulting in spaced-apart bursts of acoustic oscillations.

3. An acoustic generator as in claim 1 said signal generator including means for varying the rate of change of the frequency.

4. A method of characterizing an acoustic transducer used for the detection of acoustic emissions, comprising the steps of:
   detecting an actually occurring acoustic emission;
   providing a presentation of the frequency spectrum of the emission;
   providing an electrical signal of a variable amplitude;
   operating a voltage controlled frequency oscillator by said signal;
   driving a transmitting acoustic transducer by the oscillator to obtain a simulation of an acoustic emission;
   receiving said simulation of an acoustic emission with the transducer being characterized; and
   providing a presentation of the frequency spectrum of said simulation of an acoustic emission received by the transducer being characterized, whereby a standard presentation is obtained which is characteristic of the transducer being characterized.

5. A method of subjecting structural parts to the influence of ultrasonic waves comprising the steps of:
   generating with a single piezoelectric transducer a plurality of separate bursts of acoustic energy over a broad band, each of said separate acoustic bursts simulating the different frequency spectrum of a different acoustic emission, and coupling said bursts to said part at a selected first location thereof; and
   detecting at a second location remote from said first location the acoustic bursts received at the second location in order to determine the modifications in said bursts due to their propagation through the structural part.

* * * * *